United States Patent
Brito et al.

(10) Patent No.: US 10,286,056 B2
(45) Date of Patent: May 14, 2019

(54) ADJUVANT NANOEMULSIONS WITH CRYSTALLISATION INHIBITORS

(75) Inventors: Luis Brito, Concord, MA (US); Manmohan Singh, Cary, NC (US); Derek O'Hagan, Winchester, MA (US)

(73) Assignee: GLAXOSMITHKLINE BIOLOGICALS S.A. (BE)

( * ) Notice: Subject to any disclaimer, the term of this patent is extended or adjusted under 35 U.S.C. 154(b) by 0 days.

(21) Appl. No.: 13/982,042

(22) PCT Filed: Jan. 27, 2012

(86) PCT No.: PCT/US2012/022871
§ 371 (c)(1),
(2), (4) Date: Sep. 5, 2013

(87) PCT Pub. No.: WO2012/103421
PCT Pub. Date: Aug. 2, 2012

(65) Prior Publication Data
US 2014/0017279 A1    Jan. 16, 2014

Related U.S. Application Data

(60) Provisional application No. 61/436,946, filed on Jan. 27, 2011.

(51) Int. Cl.
| A61K 39/39 | (2006.01) |
| A61K 39/095 | (2006.01) |
| A61K 9/107 | (2006.01) |
| A61K 31/00 | (2006.01) |
| A61K 31/4745 | (2006.01) |

(Continued)

(52) U.S. Cl.
CPC .......... *A61K 39/095* (2013.01); *A61K 9/0019* (2013.01); *A61K 9/1075* (2013.01); *A61K 31/00* (2013.01); *A61K 31/4375* (2013.01); *A61K 31/4745* (2013.01); *A61K 39/39* (2013.01);

(Continued)

(58) Field of Classification Search
None
See application file for complete search history.

(56) References Cited

U.S. PATENT DOCUMENTS

| 6,391,287 B1 | 5/2002 | Baldo et al. |
| 8,703,095 B2 | 4/2014 | Klucker et al. |

(Continued)

FOREIGN PATENT DOCUMENTS

| CA | 2004810 A1 | 6/1990 |
| DE | 19527132 A1 | 1/1997 |

(Continued)

OTHER PUBLICATIONS

Gorski et al., Distinct indirect pathways govern human NK-cell activation by TLR-7 and TLR-8 agonists, International Immunology, vol. 18, No. 7: 1115-1126 (2006).*

(Continued)

*Primary Examiner* — M Franco G Salvoza

(57) ABSTRACT

High loading of lipophilic pharmacological agents (in particular, lipophilic immunopotentiators) in oil-in-water emulsions can result in crystallisation of the lipophilic agent. To overcome this problem the invention uses an oil-in-water emulsion in combination with a crystallisation inhibitor, and this combination provides emulsions which can be loaded with high levels of lipophilic pharmacological agents.

12 Claims, 5 Drawing Sheets

(51) Int. Cl.
*A61K 9/00* (2006.01)
*A61K 31/4375* (2006.01)
*A61K 47/26* (2006.01)
*A61K 47/32* (2006.01)
*A61K 47/44* (2017.01)

(52) U.S. Cl.
CPC .............. *A61K 47/26* (2013.01); *A61K 47/32* (2013.01); *A61K 47/44* (2013.01)

(56) References Cited

U.S. PATENT DOCUMENTS

| | | | |
|---|---|---|---|
| 8,846,610 B2* | 9/2014 | Keith | C07K 7/66 514/2.9 |
| 2003/0045563 A1* | 3/2003 | Gao | A61K 9/1075 514/406 |
| 2003/0059470 A1 | 3/2003 | Muller | |
| 2005/0226878 A1* | 10/2005 | Tomai et al. | 424/145.1 |
| 2007/0249692 A1* | 10/2007 | Fort | A61K 9/1635 514/365 |
| 2009/0136543 A1* | 5/2009 | Ballou et al. | 424/206.1 |
| 2009/0291095 A1* | 11/2009 | Baker et al. | 424/184.1 |
| 2010/0278812 A1* | 11/2010 | Bergenhem | A61K 9/0043 424/130.1 |
| 2010/0285135 A1* | 11/2010 | Wendorf et al. | 424/489 |
| 2011/0195944 A1* | 8/2011 | Mura | A61K 9/0014 514/182 |
| 2011/0280949 A1* | 11/2011 | Malyala et al. | 424/501 |
| 2013/0039847 A1* | 2/2013 | Gessler | A61K 9/0078 424/1.11 |

FOREIGN PATENT DOCUMENTS

| | | |
|---|---|---|
| EP | 0372501 A2 | 6/1990 |
| EP | 0378881 B1 | 6/1993 |
| EP | 0427347 B1 | 2/1995 |
| EP | 0471177 B1 | 10/1995 |
| EP | 0594610 B1 | 9/1998 |
| WO | WO-91/01146 A1 | 2/1991 |
| WO | 199207543 A1 | 5/1992 |
| WO | WO-93/17712 A2 | 9/1993 |
| WO | WO-94/03208 A1 | 2/1994 |
| WO | WO-98/58668 A2 | 12/1998 |
| WO | WO-00/033882 A1 | 6/2000 |
| WO | WO-00/056360 A2 | 9/2000 |
| WO | WO-00/061761 A2 | 10/2000 |
| WO | WO-01/072337 A1 | 10/2001 |
| WO | WO-02/02606 A2 | 1/2002 |
| WO | WO-02/034771 A2 | 5/2002 |
| WO | WO-02/091998 A2 | 11/2002 |
| WO | WO-03/018054 A1 | 3/2003 |
| WO | WO-2005/002619 A2 | 1/2005 |
| WO | WO-2005/032582 A2 | 4/2005 |
| WO | WO-2006/089264 A2 | 8/2006 |
| WO | WO-2006/091517 A2 | 8/2006 |
| WO | WO-2006/138004 A2 | 12/2006 |
| WO | WO-2007/049155 A2 | 5/2007 |
| WO | 2007080308 A2 | 7/2007 |
| WO | WO-2008/020330 A2 | 2/2008 |
| WO | WO-2009/031043 A2 | 3/2009 |
| WO | WO-2009/104092 A2 | 8/2009 |
| WO | 2009111337 A1 | 9/2009 |
| WO | WO-2009/109860 A2 | 9/2009 |

OTHER PUBLICATIONS

Mahlen et al., "Phase Transformations in Solid Pharmaceutical Materials Studied by AFM, ESCA, DSC and SAXS," Acta Universitatis Upsaliensis. Comprehensive Summaries of Uppsala Dissertations from the Faculty of Pharmacy 314. 71 pp. Uppsala ISBN 91-554-6052-6 (2004).*
Buyukotzurk et al., "Impact of emulsion-based drug delivery systems on intestinal permeability and drug release kinetics," Journal of Controlled Release 142: 22-30 (2010).*
Jin et al., "Structures of the Toll-like Receptor Family and Its Ligand Complexes," Immunity 29: 182-191 (2008).*
Kaczanowska et al., "TLR agonists: our best frenemy in cancer immunotherapy," Journal of Leukocyte Biology vol. 93: 847-863 (2013).*
Sekikawa et al., "Inhibitory Effect of Polyvinylpyrrolidone on the Crystallization of Drugs," Chem. Pharm. Bull. 26 (1): 118-126 (1978).*
Konno et al., "Ability of Different Polymers to Inhibit the Crystallization of Amorphous Felodipine in the Presence of Moisture," Pharmaceutical Research, vol. 25, No. 4 (2007).*
Tamilvanan, S. and Benita, S., "The potential of lipid emulsion for ocular delivery of lipophilic drugs," Eur. J Pharm. Biopharm., vol. 58: 357-368 (2004).
Klang, S.H., et al., "Physicochemical Characterization and Acute Toxicity Evaluation of a Positively-charged Submicron Emulsion Vehicle," J. Pharm. Pharmacol., vol. 46: 985-993 (1994).
International Search/Written Opinion issued for PCT/US2012/022871, dated Jun. 12, 2012 (11 pages).
Jain, Piyush, et al. "Inhibition of crystallization in drug-in-adhesive-type transdermal patches" Int. J. of Pharmaceutics., 394 68-74 (2010).
Giuliani, Marzia M. et al. "A universal vaccine for serogroup B meningococcus" PNAS, 103(29) 10834-9 (2006).

* cited by examiner

ADJUVANT NANOEMULSIONS WITH CRYSTALLISATION INHIBITORS

This application is the U.S. National Phase of International Application No. PCT/US2012/022871, filed Jan. 27, 2012 and published in English, which claims the benefit of U.S. Provisional Application No. 61/436,946, filed on Jan. 27, 2011. The entire contents of the foregoing applications are incorporated herein by reference.

TECHNICAL FIELD

The invention is in the field of emulsions which are useful for delivering lipophilic pharmacological agents, such as immunopotentiators.

BACKGROUND ART

Pharmacological agents can require formulation in order to optimise their in vivo effects. For instance, they might be encapsulated or adsorbed. Appropriate formulation can provide, for instance, homogeneous dosing, improved efficacy, better pharmacokinetics, or simpler manufacturing. For example, reference 1 encapsulated indomethacin in polymeric nanoparticles, and reference 2 formulated a lipophilic muramyl dipeptide immunopotentiator with polylactide microspheres.

It is an object of the invention to provide further and improved ways of formulating lipophilic pharmacological agents for in vivo use, including methods which offer improved processing during manufacture when compared to simple monodispersions of the lipophilic agent.

DISCLOSURE OF THE INVENTION

The inventors attempted to formulate lipophilic pharmacological agents (in particular, lipophilic immunopotentiators) in oil-in-water emulsions, but the emulsions could accommodate only low concentrations of agent. Higher loading led to crystallisation of the lipophilic agent, which gives an undesirably unstable emulsion. To overcome this observed crystallisation the invention uses an oil-in-water emulsion in combination with a crystallisation inhibitor, and this combination provides emulsions which can be loaded with high levels of lipophilic pharmacological agents.

Thus the invention provides an oil-in-water emulsion comprising an aqueous phase, an oil phase, a surfactant, and a crystallisation inhibitor. These emulsions are useful for formulating lipophilic pharmacological agents for in vivo use, and so the invention also provides an oil-in-water emulsion comprising an aqueous phase, an oil phase, a surfactant, a crystallisation inhibitor, and a lipophilic pharmacological agent.

The invention also provides an immunogenic composition comprising (a) an oil-in-water emulsion of the invention and (b) an immunogen.

The invention also provides a process for preparing an oil-in-water emulsion, comprising a step of homogenising a mixture comprising an aqueous component, an oil component, and a surfactant component, wherein a crystallisation inhibitor is added to the mixture before, during or after homogenisation (preferably before). A lipophilic pharmacological agent may be added (i) to the mixture before during or after homogenisation, or (ii) to the emulsion before or after addition of the crystallisation inhibitor; it is preferably added to the mixture before homogenisation and before addition of the crystallisation inhibitor. The homogenisation may comprise microfluidisation.

The invention also provides a process for preparing an immunogenic composition, comprising a step of mixing an immunogen with an emulsion of the invention.

Lipophilic Pharmacological Agents

Emulsions of the invention are useful for formulating lipophilic pharmacological agents (LPAs) for in vivo use. Such LPAs include, but are not limited to, vitamins (e.g. vitamins A, D, E and K and their salts/esters, such as α-tocopherol succinate), carotenoids (e.g. β-carotene), fatty acids (e.g. arachidonic acid, ecosapentaenoic acid docosahexaenoic acid), pyrimidines (e.g. 5-hydroxy-4,6-dimethyl-2-(6-phenylhexyl)aminopyrimidine), ansamitocins, angiotensin II receptor antagonists (e.g. candesartan cilexetil), and immunopotentiators (e.g. muramyl dipeptides). Typical LPAs have a positive log P value (partition coefficient measured in 1-octanol and water) at pH 7.4 and 37° C. e.g. they may have a log P value $\geq 1$, $\geq 2$, $\geq 3$, $\geq 4$, $\geq 5$, $\geq 6$, $\geq 7$, etc.

The invention is particularly useful for formulating LPAs which can crystallise. Thus it is useful for LPAs that crystallise when present in an oil-in-water emulsion which is identical to an emulsion of the invention except for absence of the crystallisation inhibitor (i.e. the same aqueous phase, oil phase, surfactant and LPA as an emulsion of the invention, in the same amounts, but lacking the crystallisation inhibitor).

Preferred LPAs for use with the invention are small molecule immune potentiators (SMIPs). These SMIPs have a molecular weight of less than 5000 Da (e.g. <4000 Da, <3000 Da, <2000 Da, or <1000 Da). They may function as agonists of one or more of human toll-like receptors TLR1, TLR2, TLR3, TLR4, TLR5, TLR6, TLR7, TLR8, TLR9 and/or TLR11, or may agonise other receptors such as CD1d. Lipophilic agonists of TLR1 include lipopeptides. Lipophilic agonists of TLR2 include glycolipids and lipoteichoic acid.

Lipophilic agonists of TLR7 include the naphthyridines disclosed in reference 3. Specific lipophilic SMIPs for use with the invention include, but are not limited to, the compounds disclosed in the examples of reference 3 e.g. example 161 (compound 'A' herein). Compound 'A' are very lipophilic and highly crystalline.

Emulsions of the invention may include only one LPA or may include multiple LPAs.

In preferred emulsions, most or all (e.g. $\geq 80\%$, $\geq 85\%$, $\geq 90\%$, $\geq 95\%$) of the total LPA is present (dissolved) in the emulsion's oil droplets.

The concentration of LPA in an emulsion of the invention can vary over a wide range e.g. between 10 µg/ml to 50 mg/ml, between 0.1 mg/ml to 5 mg/ml, or between 0.5 mg/ml to 2 mg/ml.

Crystallisation Inhibitors

Emulsions of the invention include a crystallisation inhibitor. Various such inhibitors are known in the art. For instance, an emulsion of the invention may include a polyvinylpyrrolidone (PVP), a hydroxypropylmethylcellulose (HPMC), a poloxamer, a dextrin derivative, a polyethylene glycol (PEG), a polypropylene glycol (PPG), a polyvinyl acetate (PVA), a copolymer of vinylpyrrolidone and vinyl acetate, or glycerin [4-6]. Preferred crystallisation inhibitors are polymers.

PVP is a water-soluble polymer formed from N-vinylpyrrolidone monomers. Useful PVPs can have a K value (Fikentscher's viscosity coefficient) between 10-150 e.g. between 12-100, between 12-20, or between 15-30. One useful PVP has a K value of 15.

Useful HPMCs include salts or esters such as hydroxypropyl methylcellulose acetate succinate.

Poloxamers are non-ionic copolymers with a central hydrophobic chain of polyoxypropylene flanked by two hydrophilic chains of polyoxyethylene. Useful poloxamers for crystallisation inhibition include poloxamer "407" (Lutrol 127) [6].

Useful crystallisation inhibitors are typically amorphous e.g. PVP.

The amount of a crystallisation inhibitor in an emulsion of the invention can vary widely but will depend on the LPA in question and its desired dose. The amount of crystallisation inhibitor in the emulsion will be enough to ensure that substantially all of the LPA remains amorphous for the emulsion's desired shelf life with an adequate LPA loading.

Emulsions of the invention may include only one crystallisation inhibitor or may include multiple crystallisation inhibitors.

The crystallisation inhibitor will usually be located in the emulsion's oil phase, although it may also be present in the aqueous phase.

Oil-in-water Emulsions

Emulsions of the invention comprise oil droplets in an aqueous bulk phase. The emulsions include a surfactant and this can facilitate formation and stabilisation of the emulsion.

The emulsion may comprise one or more oils and/or fatty acids. Suitable oil(s) include those from, for example, an animal (such as fish) or a vegetable source. The oil is ideally biodegradable (metabolisable) and biocompatible. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and so may be used. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Squalane, the saturated analog to squalene, can also be used. Fish oils, including squalene and squalane, are readily available from commercial sources or may be obtained by methods known in the art.

Other useful oils are the tocopherols, particularly in combination with squalene. Where the oil phase of an emulsion includes a tocopherol, any of the α,β, γ, δ, ε or ξ tocopherols can be used, but α-tocopherols are preferred. D-α-tocopherol and DL-α-tocopherol can both be used. A preferred α-tocopherol is DL-α-tocopherol. An oil combination comprising squalene and a tocopherol (e.g. DL-α-tocopherol) can be used.

Preferred emulsions comprise squalene, a shark liver oil which is a branched, unsaturated terpenoid ($C_{30}H_{50}$; [($CH_3$)$_2$C [=$CHCH_2CH_2C(CH_3$)]$_2$=$CHCH_2$—]$_2$; 2,6,10,15,19,23-hexamethyl-2,6,10,14,18,22-tetracosahexaene; CAS RN 7683-64-9).

The oil in the emulsion may comprise a combination of oils e.g. squalene and at least one further oil.

The aqueous component of the emulsion can be plain water (e.g. w.f.i.) or can include further components e.g. solutes. For instance, it may include salts to form a buffer e.g. citrate or phosphate salts, such as sodium salts. Typical buffers include: a phosphate buffer; a Tris buffer; a borate buffer; a succinate buffer; a histidine buffer; or a citrate buffer. A buffered aqueous phase is preferred, and buffers will typically be included in the 5-20 mM range.

The surfactant in the emulsion is preferably biodegradable (metabolisable) and biocompatible. Surfactants can be classified by their 'HLB' (hydrophile/lipophile balance), where a HLB in the range 1-10 generally means that the surfactant is more soluble in oil than in water, and a HLB in the range 10-20 are more soluble in water than in oil. Emulsions preferably comprise at least one surfactant that has a HLB of at least 10 e.g. at least 15, or preferably at least 16.

The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy) polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the Spans), such as sorbitan trioleate (Span 85) and sorbitan monolaurate. Preferred surfactants for including in the emulsion are polysorbate 80 (Tween 80; polyoxyethylene sorbitan monooleate), Span 85 (sorbitan trioleate), lecithin and Triton X-100.

Mixtures of surfactants can be included in the emulsion e.g. Tween 80/Span 85 mixtures, or Tween 80/Triton-X100 mixtures. A combination of a polyoxyethylene sorbitan ester such as polyoxyethylene sorbitan monooleate (Tween 80) and an octoxynol such as t-octylphenoxy-polyethoxyethanol (Triton X-100) is also suitable. Another useful combination comprises laureth-9 plus a polyoxyethylene sorbitan ester and/or an octoxynol. Useful mixtures can comprise a surfactant with a HLB value in the range of 10-20 (e.g. polysorbate 80, with a HLB of 15.0) and a surfactant with a HLB value in the range of 1-10 (e.g. sorbitan trioleate, with a HLB of 1.8).

In addition to the oil, aqueous and surfactant components, an emulsion can include further components. For instance, an emulsion can include cholesterol and/or a phospholipid. Inclusion of a phospholipid can increase the loading capacity of an emulsion. Suitable classes of phospholipid include, but are not limited to, phosphatidylethanolamines, phosphatidylcholines, phosphatidylserines, phosphatidylglycerols, etc. Useful phospholipids are listed in Table 1. These phospholipid components will typically be present in an emulsion's oil phase.

Preferred amounts of oil (% by volume) in the final emulsion are between 2-20% e.g. 5-15%, 6-14%, 7-13%, 8-12%. A squalene content of about 4-6% or about 9-11% is particularly useful.

Preferred amounts of surfactants (% by weight) in the final emulsion are between 0.001% and 8%. For example: polyoxyethylene sorbitan esters (such as polysorbate 80) 0.2 to 4%, in particular between 0.4-0.6%, between 0.45-0.55%, about 0.5% or between 1.5-2%, between 1.8-2.2%, between 1.9-2.1%, about 2%, or 0.85-0.95%, or about 1%; sorbitan esters (such as sorbitan trioleate) 0.02 to 2%, in particular about 0.5% or about 1%; octyl- or nonylphenoxy polyoxyethanols (such as Triton X-100) 0.001 to 0.1%, in particular 0.005 to 0.02%; polyoxyethylene ethers (such as laureth 9) 0.1 to 8%, preferably 0.1 to 10% and in particular 0.1 to 1% or about 0.5%.

The absolute amounts of oil and surfactant, and their ratio, can be varied within wide limits while still forming an emulsion. A skilled person can easily vary the relative proportions of the components to obtain a desired emulsion, but a weight ratio of between 4:1 and 5:1 for oil and surfactant is typical (excess oil). The amounts of cholesterol and/or phospholipid can similarly be varied widely while obtaining a desired emulsion e.g. between 0.5 mg/ml and 20 mg/ml e.g. between 2-10 mg/ml, or between 3-7 mg/ml, or about 5 mg/ml. The amounts of these various components may be selected to provide a useful formulation of the relevant LPA e.g. to ensure that there is sufficient oil to dissolve the desired dose of LPA, etc., while giving a stable emulsion with high LPA loading.

An important parameter for ensuring immunostimulatory activity of an emulsion, particularly in large animals, is the oil droplet size (diameter). The most effective emulsions have a droplet size in the submicron range. Suitably the droplet sizes will be in the range 50-750 nm. Most usefully the average droplet size is less than 250 nm e.g. less than 200 nm, less than 150 nm. The average droplet size is usefully in the range of 80-180 nm. Ideally, at least 80% (by number) of the emulsion's oil droplets are less than 250 nm in diameter, and preferably at least 90%. Apparatuses for determining the average droplet size in an emulsion, and the size distribution, are commercially available. These these typically use the techniques of dynamic light scattering and/or single-particle optical sensing e.g. the Accusizer™ and Nicomp™ series of instruments available from Particle Sizing Systems (Santa Barbara, USA), or the Zetasizer™ instruments from Malvern Instruments (UK), or the Particle Size Distribution Analyzer instruments from Horiba (Kyoto, Japan).

Ideally, the distribution of droplet sizes (by number) has only one maximum i.e. there is a single population of droplets distributed around an average (mode), rather than having two maxima. Preferred emulsions have a polydispersity of <0.4 e.g. 0.3 or less.

Suitable emulsions with submicron droplets and a narrow size distribution can be obtained by the use of microfluidisation. This technique reduces average oil droplet size by propelling streams of input components through geometrically fixed channels at high pressure and high velocity. These streams contact channel walls, chamber walls and each other. The results shear, impact and cavitation forces cause a reduction in droplet size. Repeated steps of microfluidisation can be performed until an emulsion with a desired droplet size average and distribution are achieved.

As an alternative to microfluidisation, thermal methods can be used to cause phase inversion, as disclosed in reference 7. These methods can also provide a submicron emulsion with a tight particle size distribution.

Preferred emulsions can be filter sterilised i.e. their droplets can pass through a 220 nm filter. As well as providing a sterilisation, this procedure also removes any large droplets in the emulsion.

Preferred emulsions are adjuvant emulsions i.e. they can provide an in vivo immunostimulatory effect in a mammal even if administered without the lipophilic agent and without the crystallisation inhibitor. Known adjuvant emulsions, in which a lipophilic agent and a crystallisation inhibitor can be incorporated, include:

An emulsion comprising squalene, polysorbate 80 (Tween 80), and sorbitan trioleate (Span 85). The composition of the emulsion by volume can be about 5% squalene, about 0.5% polysorbate 80 and about 0.5% sorbitan trioleate. In weight terms, these amounts become 4.3% squalene, 0.5% polysorbate 80 and 0.48% sorbitan trioleate. This adjuvant is known as 'MF59'. The MF59 emulsion advantageously includes citrate ions e.g. 10 mM sodium citrate buffer.

Emulsions comprising squalene, an α-tocopherol (ideally DL-α-tocopherol), and polysorbate 80. These emulsions may have (by weight) from 2 to 10% squalene, from 2 to 10% α-tocopherol and from 0.3 to 3% polysorbate 80 e.g. 4.3% squalene, 4.7% α-tocopherol, 1.9% polysorbate 80. The weight ratio of squalene: tocopherol is preferably ≤1 (e.g. 0.90) as this provides a more stable emulsion. Squalene and polysorbate 80 may be present volume ratio of about 5:2, or at a weight ratio of about 11:5. One such emulsion can be made by dissolving polysorbate 80 in PBS to give a 2% solution, then mixing 90 ml of this solution with a mixture of (5 g of DL-α-tocopherol and 5 ml squalene), then microfluidizing the mixture. The resulting emulsion may have submicron oil droplets e.g. with an average diameter of between 100 and 250 nm, preferably about 180 nm.

An emulsion comprising squalene, a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include a 3d-MPL. The emulsion may also include a saponin, such as QS21. The aqueous phase may contain a phosphate buffer.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [7]. The emulsion may also include one or more of: alditol; a cryoprotective agent (e.g. a sugar, such as dodecylmaltoside and/or sucrose); and/or an alkylpolyglycoside. It may also include a TLR4 agonist, such as one whose chemical structure does not include a sugar ring [8]. Such emulsions may be lyophilized.

Immunogens

Where the LPA is an immune potentiator, emulsions of the invention are useful for co-delivery with immunogens, thereby providing enhanced immunogenicity. Thus an immunogenic composition of the invention can comprise a SMIP-containing emulsion of the invention and an immunogen.

The immunogen may elicit an immune response against a bacterium, a virus, a fungus or a parasite. As an alternative to eliciting an immune response against a pathogen, the immunogen may be a self antigen for immunotherapy e.g. a cancer antigen.

Bacterial immunogens can comprise proteins, saccharides, and/or lipopolysaccharides. They may be live bacteria, inactivated bacteria, or bacterial subunits. Examples of useful immunogens elicit an immune response against:

*Neisseria meningitidis*: useful immunogens include, but are not limited to, membrane proteins and/or capsular saccharides. Capsular saccharides from serogroups A, C, W135, and/or Y are useful. Adhesins, autotransporters, toxins, iron acquisition proteins, and factor H binding proteins are useful membrane protein immunogens. A preferred vaccine includes the protein antigens disclosed in reference 9.

*Streptococcus pneumoniae*: useful immunogens include, but are not limited to, proteins and/or capsular saccharides. For example, capsular saccharides from any of pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and/or 33F can be used.

*Streptococcus pyogenes*: useful immunogens include, but are not limited to, proteins and/or capsular saccharides. Useful proteins are disclosed in references 10 and 11.

*Moraxella catarrhalis.*

*Bordetella pertussis*: Useful pertussis immunogens include, but are not limited to, pertussis toxin or toxoid (PT), filamentous haemagglutinin (FHA), pertactin, and agglutinogens 2 and 3.

*Staphylococcus aureus*: Useful immunogens include, but are not limited to, proteins and/or capsular saccharides. For example, type 5 and/or type 8 capsular saccharides can be used.

*Clostridium tetani*: The typical immunogen is tetanus toxoid.

*Cornynebacterium diphtheriae*: the typical immunogen is diphtheria toxoid.

*Haemophilus influenzae* type B: the typical Hib immunogen is its capsular saccharide, PRP.

*Pseudomonas aeruginosa*

*Streptococcus agalactiae*: useful immunogens include, but are not limited to, proteins and/or capsular saccharides. Useful proteins are disclosed in reference 12. Capsular saccharides from one or more of serotypes Ia, Ib, Ia/c, II, III, IV, V, VI, VII and VIII can be used.

*Chlamydia trachomatis*: Useful immunogens include, but are not limited to, PepA, LcrE, ArtJ, DnaK, CT398, OmpH-like, L7/L12, OmcA, AtoS, CT547, Eno, HtrA and MurG (e.g. as disclosed in reference 13. LcrE [14] and HtrA [15] are two preferred immunogens.

*Chlamydia pneumoniae*: Useful immunogens include, but are not limited to, the proteins disclosed in reference 16.

*Helicobacter pylori*: Useful immunogens include, but are not limited to, CagA, VacA, NAP, and/or urease [17].

*Escherichia coli*: Useful immunogens include, but are not limited to, immunogens derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC strains include uropathogenic *E. coli* (UPEC) and meningitis/sepsis-associated *E. coli* (MNEC). Useful UPEC immunogens are disclosed in references 18 and 19. Useful MNEC immunogens are disclosed in reference 20. A useful immunogen for several *E. coli* types is AcfD [21].

*Bacillus* anthracia

*Yersinia pestis*: Useful immunogens include, but are not limited to, those disclosed in references 22 and 23.

*Salmonella typhi*: the typical *S. typhi* immunogen is its capsular saccharide, Vi.

Where the immunogen is a saccharide, it will usually be conjugated to a carrier protein. For example, pneumococcal, Hib, *S. aureus, S. typhi* and meningococcal saccharide conjugate vaccines are known in the art. Carrier proteins are typically a bacterial toxin or toxoid (e.g. a diphtheria or tetanus toxoid, or a non-toxic mutant form thereof e.g. CRM197 [24]), but other carriers can be used. For example, suitable carrier proteins include but are not limited to: *N. meningitidis* outer membrane protein complex [25], synthetic peptides [26,27], heat shock proteins [28,29], pertussis proteins [30,31], cytokines [32], lymphokines [32], hormones [32], growth factors [32], artificial proteins comprising multiple human $CD4^+$ T cell epitopes from various pathogen-derived antigens [33] such as N19 [34], protein D from *H. influenzae* [35-37], iron-uptake proteins [38], toxin A or B from *C. difficile* [39], recombinant *P. aeruginosa* exoprotein A (rEPA) [40], pneumolysin [41] or its non-toxic derivatives [42], pneumococcal surface protein PspA [43], etc.

Viral immunogens can comprise proteins. They may be live viruses, inactivated viruses, or viral subunits. Examples of useful immunogens elicit an immune response against:

Orthomyxovirus: Useful immunogens can be from an influenza A, B or C virus. A live attenuated virus or an inactivated virus can be used, including a whole inactivated virus, a split virus, or viral surface glycoproteins (including hemagglutinin). The vaccine may be monovalent, 2-valent, 3-valent, 4-valent or more.

Paramyxoviridae viruses: Viral immunogens include, but are not limited to, those derived from Pneumoviruses (e.g. respiratory syncytial virus), Paramyxoviruses (e.g. parainfluenza virus), Metapneumoviruses and Morbilliviruses (e.g. measles).

Poxyiridae: Viral immunogens include, but are not limited to, those derived from Orthopoxvirus such as Variola vera, including but not limited to, Variola major and Variola minor.

Picornavirus: Viral immunogens include, but are not limited to, those derived from Picornaviruses, such as Enteroviruses, Rhinoviruses, Heparnavirus, Cardioviruses and Aphthoviruses. In one embodiment, the enterovirus is a poliovirus e.g. a type 1, type 2 and/or type 3 poliovirus.

Bunyavirus: Viral immunogens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Heparnavirus: Viral immunogens include, but are not limited to, those derived from a Heparnavirus, such as hepatitis A virus (HAV).

Togavirus: Viral immunogens include, but are not limited to, those derived from a Togavirus, such as a Rubivirus, an Alphavirus, or an Arterivirus. This includes rubella virus.

Flavivirus: Viral immunogens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus.

Pestivirus: Viral immunogens include, but are not limited to, those derived from a Pestivirus, such as Bovine viral diarrhea (BVDV), Classical swine fever (CSFV) or Border disease (BDV).

Hepadnavirus: Viral immunogens include, but are not limited to, those derived from a Hepadnavirus, such as Hepatitis B virus. A composition can include hepatitis B virus surface antigen (HBsAg).

Other hepatitis viruses: A composition can include an immunogen from a hepatitis C virus, delta hepatitis virus, hepatitis E virus, or hepatitis G virus.

Rhabdovirus: Viral immunogens include, but are not limited to, those derived from a Rhabdovirus, such as a Lyssavirus (Rabies virus) and Vesiculovirus (VSV).

Caliciviridae: Viral immunogens include, but are not limited to, those derived from Calciviridae, such as Norwalk virus, and Norwalk-like Viruses, such as Hawaii Virus and Snow Mountain Virus.

Coronavirus: Viral immunogens include, but are not limited to, those derived from a SARS coronavirus, avian infectious bronchitis (IBV), Mouse hepatitis virus (MHV), and Porcine transmissible gastroenteritis virus (TGEV). The coronavirus antigens may comprise spike protein.

Retrovirus: Viral immunogens include, but are not limited to, those derived from an Oncovirus, a Lentivirus or a Spumavirus.

Reovirus: Viral immunogens include, but are not limited to, those derived from an Orthoreovirus, a Rotavirus, an Orbivirus, or a Coltivirus.

Parvovirus: Viral immunogens include, but are not limited to, those derived from Parvovirus B19.

Herpesvirus: Viral immunogens include, but are not limited to, those derived from a human herpesvirus, such as, by way of example only, Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: Viral immunogens include, but are not limited to, those derived from Papillomaviruses and Polyomaviruses. The Papillomavirus may be of serotype 1, 2, 4, 5, 6, 8, 11, 13, 16, 18, 31, 33, 35, 39, 41, 42, 47, 51, 57, 58, 63 or 65 e.g. from one or more of serotypes 6, 11, 16 and/or 18.

Adenovirus: Viral immunogens include those derived from adenovirus serotype 36 (Ad-36).

Fungal immunogens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. album, var. discoides, var. ochraceum, *Trichophyton violaceum,* and/or *Trichophyton faviforme*; or from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Emulsion Formation

Emulsions of the invention can be made by various methods. As mentioned above, microfluidisation or phase inversion can be used to provide emulsions with small oil droplets. Ideally the emulsion's components are combined before these techniques are used e.g. such that all of components are microfluidised together. In other embodiments, though, an emulsion may be formed from the aqueous, surfactant and oil components, and then the LPA and crystallisation inhibitor can be added. Usually the LPA and crystallisation inhibitor are added to the oil, and this oily mixture is combined with the aqueous component prior to microfluidisation, with surfactant being added either as a third component or as part of the oily or aqueous component. Other orders of mixing can also be used. In general, an immunogen will be added after an emulsion is formed e.g. after microfluidisation.

One method for forming the emulsion comprises combining aqueous, oil and surfactant components with an organic solution of the LPA e.g. in a volatile organic solvent such as dichloromethane or methylene chloride. The volatile solvent can then be evaporated e.g. after homogenisation of the mixture. After evaporation the homogenised mixture can be microfluidised.

Pharmaceutical Compositions and Products

Emulsions and immunogenic compositions of the invention are for in vivo use (in humans or animals) and so should include only pharmaceutically acceptable components. Useful pharmaceutical components, such as carrier(s) and/or excipient(s), are discussed in reference 44.

Pharmaceutical compositions may include one or more preservatives, such as thiomersal or 2-phenoxyethanol. Mercury-free compositions are preferred, and preservative-free vaccines can be prepared.

Pharmaceutical compositions can have an osmolality of between 200 mOsm/kg and 400 mOsm/kg, e.g. between 240-360 mOsm/kg, or between 290-310 mOsm/kg.

Pharmaceutical compositions typically have a pH between 5.0 and 9.5 e.g. between 6.0 and 8.0.

Pharmaceutical compositions are preferably sterile.

Pharmaceutical compositions preferably non-pyrogenic e.g. containing <1 EU (endotoxin unit, a standard measure) per dose, and preferably <0.1 EU per dose.

Pharmaceutical compositions are preferably gluten free.

Pharmaceutical compositions of the invention may be prepared in unit dose form. In some embodiments a unit dose may have a volume of between 0.1-1.0 ml e.g. about 0.5 ml.

The compositions may be prepared as injectables e.g. for intramuscular injection.

Methods of Treatment and Medical Uses

The invention provides a method for raising an immune response in a mammal comprising the step of administering an effective amount of an immunogenic composition of the invention. The immune response is preferably protective and preferably involves antibodies and/or cell-mediated immunity. The method may raise a booster response.

The invention also provides an emulsion or immunogenic composition of the invention for use in raising an immune response in a mammal.

The invention also provides the use of an emulsion or immunogenic composition of the invention in the manufacture of a medicament for raising an immune response in a mammal.

By raising an immune response in the mammal by these uses and methods, the mammal can be protected against various diseases and/or infections e.g. against bacterial and/or viral diseases as discussed above.

The invention also provides a delivery device containing an immunogenic composition of the invention. This device can be used to administer the composition to a mammalian subject.

The mammal is preferably a human. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal or transcutaneous, intranasal, ocular, aural, pulmonary or other mucosal administration.

The invention may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, multiple doses may be administered approximately 6 weeks, 10 weeks and 14 weeks after birth, e.g. at an age of 6 weeks, 10 weeks and 14 weeks, as often used in the World Health Organisation's Expanded Program on Immunisation ("EPI"). In an alternative embodiment, two primary doses are administered about two months apart, e.g. about 7, 8 or 9 weeks apart, followed by one or more booster doses about 6 months to 1 year after the second primary dose, e.g. about 6, 8, 10 or 12 months after the second primary dose. In a further embodiment, three primary doses are administered about two months apart, e.g. about 7, 8 or 9 weeks apart, followed by one or more booster doses about 6 months to 1 year after the third primary dose, e.g. about 6, 8, 10, or 12 months after the third primary dose.

Vaccines prepared according to the invention may be used to treat both children and adults. Thus a human patient may be less than 1 year old, less than 5 years old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

MODES FOR CARRYING OUT THE INVENTION

Reference 3 discloses a series of TLR7 agonist naphthyridines, including compound 'A' (example 161 on page 269):

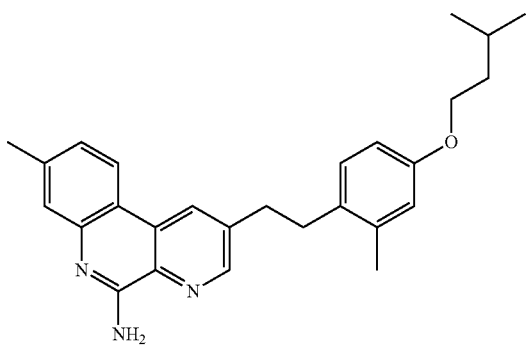 [SMILES: Cc1ccc2c(c1)nc(N)c1ncc(CCc3ccc(OCCC(C)C)cc3C)cc12]

Although these compounds are highly lipophilic (e.g. log P of compound 'A' is 7.5) they are not soluble in oil at concentrations which would be desirable for in vivo use. For example, to deliver a 25 µg dose in a typical oil-in-water emulsion would require the agonist to have a squalene solubility of 10 mg/ml, which is about 2.5× higher than can be achieved.

Figure 1:
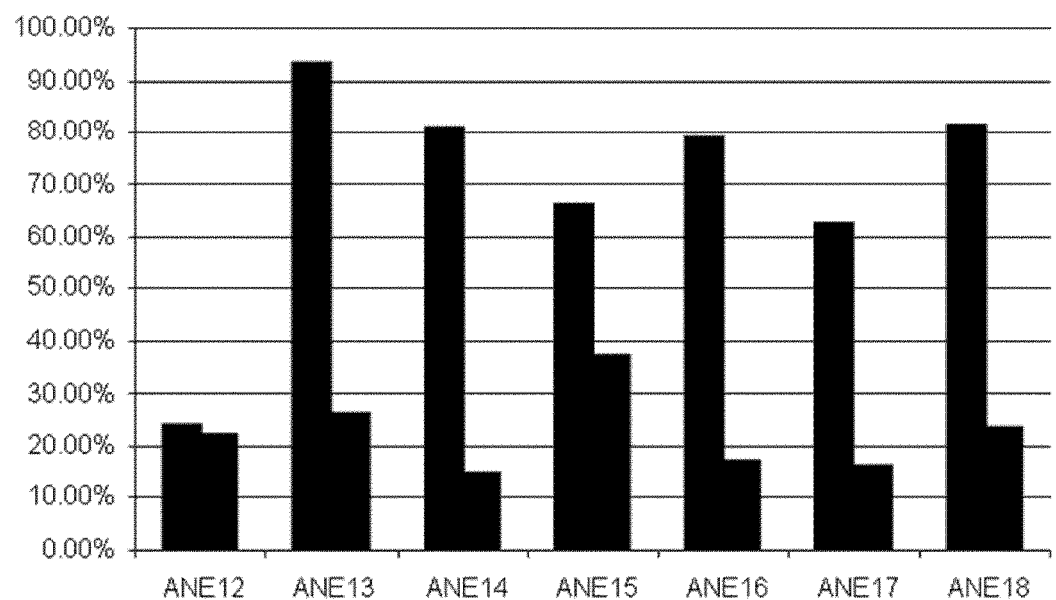
FIG. 1 shows % recovery of compound 'A' agonist in emulsions ANE12 to ANE18, both before (hatched) and after (white) centrifugation.
Figure 2A:
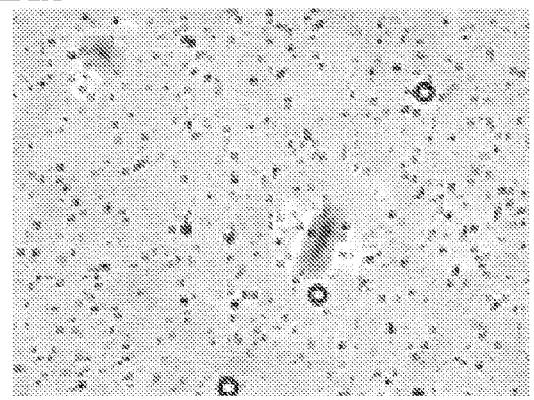
FIG. 2 shows microscope images of emulsions (A) ANE05 (B) ANE31 (C) ANE32 and (D) MF59.
Figure 2B:
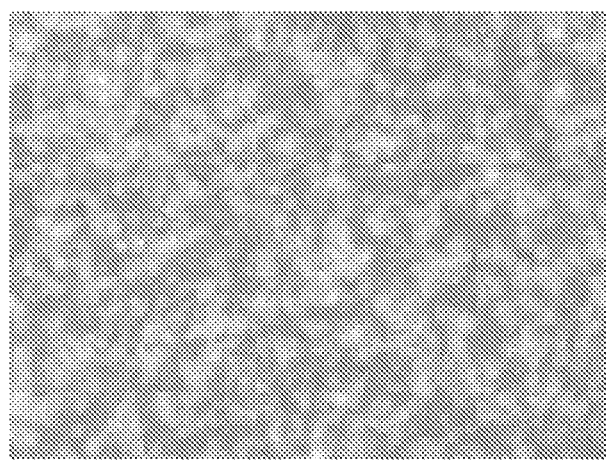
Figure 2C:
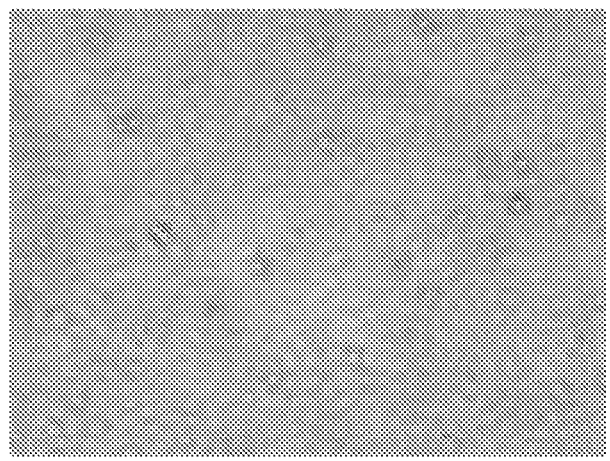
Figure 2D:
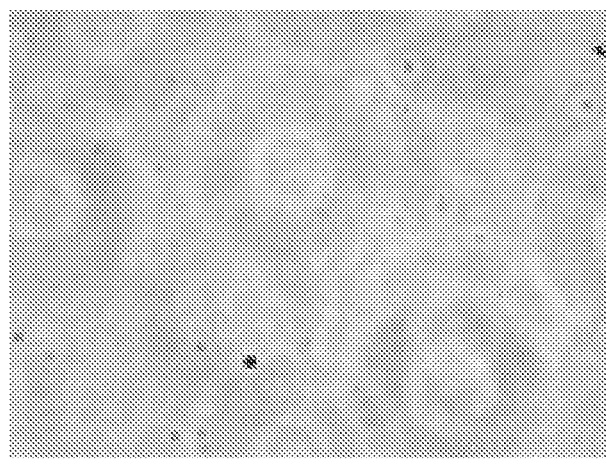

Lipids were added to the MF59 emulsion in an attempt to increase its capacity for solubilising the agonists. A variety of different phospholipid chain lengths (POPC, DLPC, DMPC, DSPC; emulsions "ANE06" to "ANE10") were tested at a 25 µg dose of agonist, and also cholesterol. These emulsions were visually stable, and provided high loading (essentially 100%), but after storage at room temperature the particle size was observed to grow. Further investigation revealed that the agonist was crystallising within the emulsion. Emulsions ANE12 to ANE18 were tested by HPLC for agonist content before and after centrifugation to separate small and large droplets. A lower value after centrifugation indicates that the agonist was dissolved in larger unstable droplets. As shown in FIG. 1, although the addition of lipids increased loading compared to ANE12, recovery dropped for all of the emulsions, indicating that the extra agonist was crystallising and causing emulsion instability.

As the emulsion was unstable, various attempts were made to prevent crystallization of the agonist within the oil phase. PVP was added as a crystallisation inhibitor, at various amounts from 2.5 mg/ml up to 10 mg/ml (ANE19 to ANE25). Loading was high (≥80%) and agonist content was substantially the same before and after centrifugation i.e. the PVP was preventing crystallisation of the agonist.

Emulsions ANE05 and ANE19 to ANE24 were stored at room temperature for a week to accelerate any crystallisation which might occur. The content of compound 'A' dropped by about 15% in the control emulsion ANE05, but was stable in the other emulsions, showing that PVP prevents crystallisation for at least a week.

Emulsions ANE31 to ANE38 were used to study the effect of adding phospholipid (DSPC) or cholesterol together with PVP. ANE32 (DSPC and PVP) had the highest loading before and after 1 week at room temperature. PVP alone increased stability but did not increase loading (ANE33).

FIG. 2 shows emulsions ANE05, ANE31 and ANE32 after 1 week at room temperature, compared to MF59 (2D). ANE31 is more disperse than ANE05, but aggregates are still present. In contrast, ANE32 with DSPC and PVP is visibly more stable.

Figure 5:
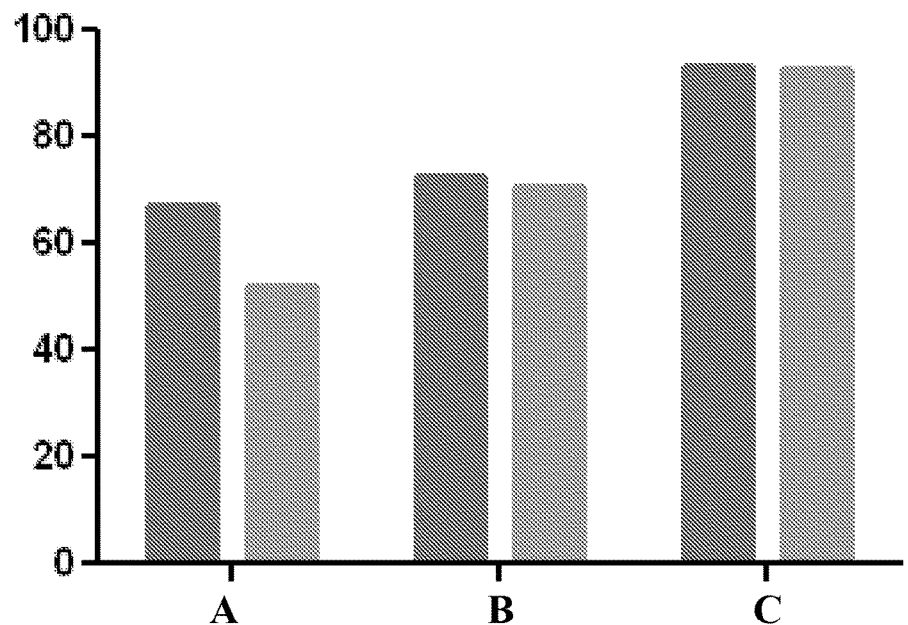
FIG. 5 shows HPLC recovery of compound 'A' from (A) ANE03, (B) ANE31 and (C) ANE32. For each pair of bars the left is recovery at time zero and the right after 7 days at room temperature.

FIG. 5 shows HPLC recovery of compound 'A' from ANE05, ANE31 and ANE32. Recovery is both higher and more stable in ANE32.

The following table summarises the effect of the various components added to the starting emulsion:

|  | "Blank" Emulsion | +lipid | +cholesterol | +PVP | +lipid +PVP | +cholesterol +PVP | +lipid +cholesterol +PVP |
|---|---|---|---|---|---|---|---|
| Loading | ~70% | ~100% | ~100% | ~80% | ~95% | ~85% | ~85% |
| Stable | No | No | No | Yes | Yes | Yes | Yes |

Thus addition of phospholipids or cholesterol (5 mg/ml) increased loading of the emulsions but did not improve stability (assessed by droplet size and by microscopy). Addition of PVP improved stability and gave a small increase in loading. Addition of cholesterol and PVP further increased loading, and very high loading was seen with a combination of phospholipid and PVP.

Pharmacokinetics

Figure 3A:
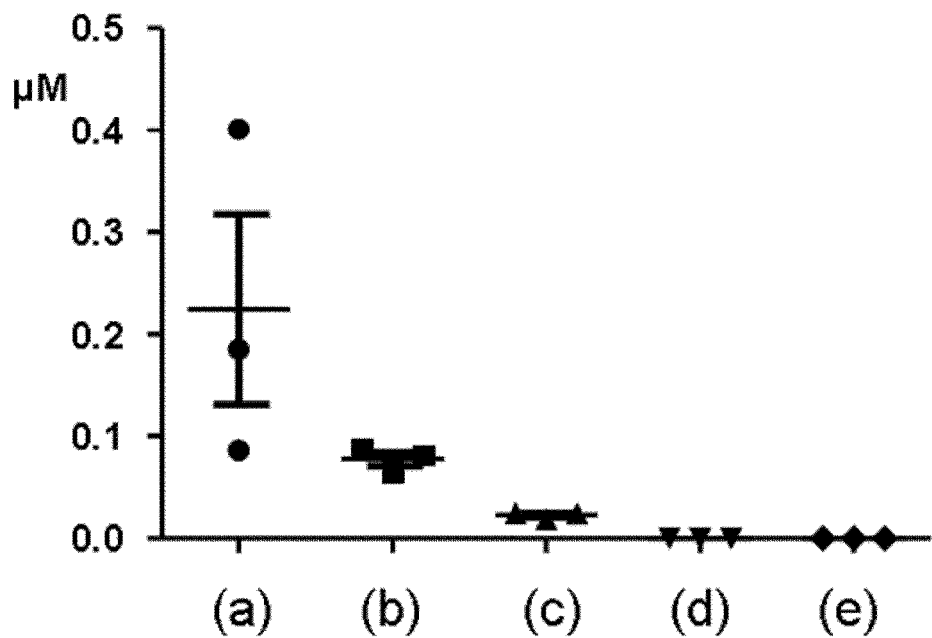
FIG. 3 shows levels of compound 'A' in (A) liver, (B) muscle and (C) serum. Values are in μM.
Figure 3B:
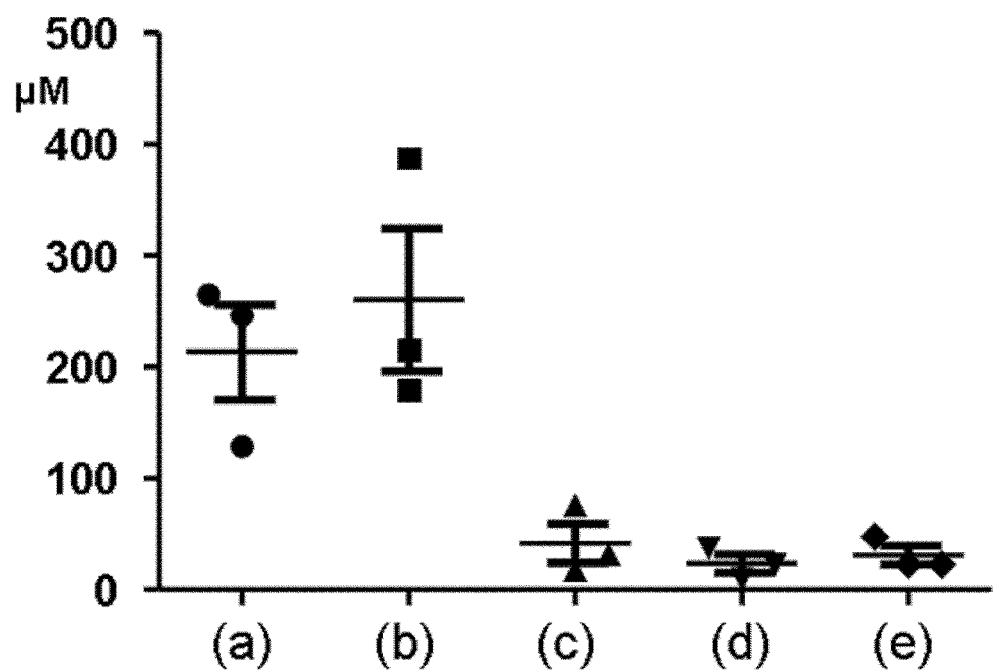

Levels of compound 'A' were assessed in liver and muscle for five groups of mice: (a) simple monodispersion of compound 'A'; (b) monodispersion and separately administered emulsion; (c) ANE05; (d) ANE31; and (e) ANE32. As shown in FIG. 3A, liver levels are the highest in group (a), and then fall through (b) to (e), but are very low in all groups. Muscle levels (FIG. 3B) are higher in groups (a) and (b) than in groups (c) to (e). Incorporation of compound 'A' in the emulsion's oil phase thus seems to clear the drug from the muscle.

Figure 3C:
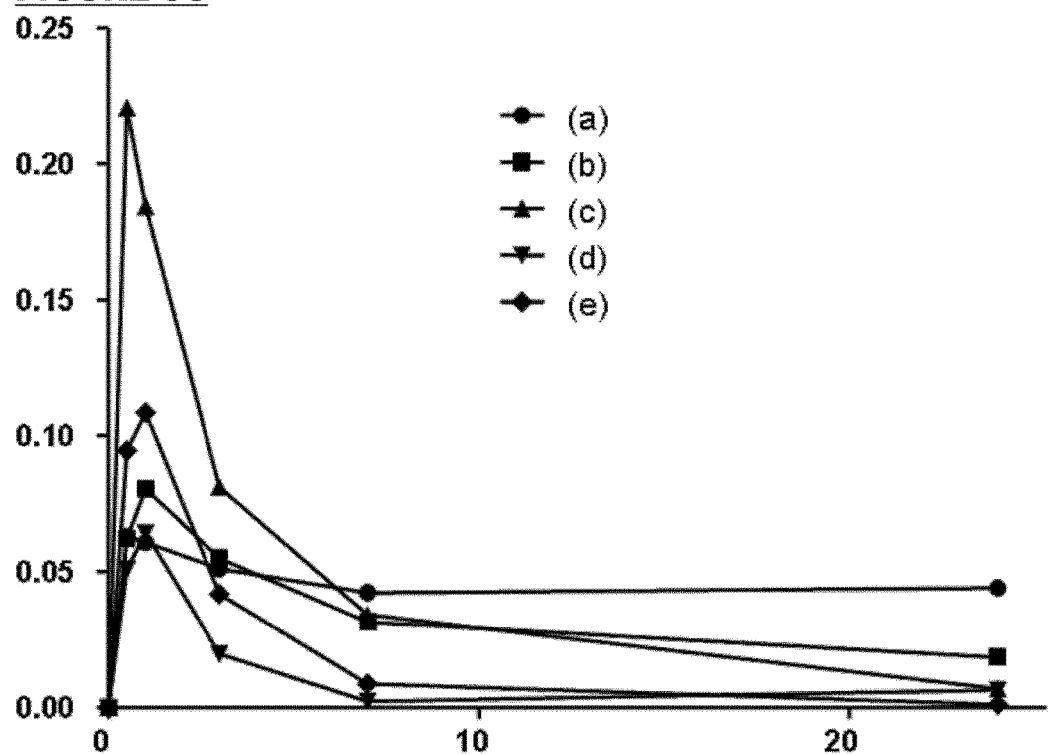

Serum levels were also monitored (FIG. 3C). After 24 hours levels for groups (a) and (b) are higher than for (c) to (e) but are again very low.

Figure 4A:
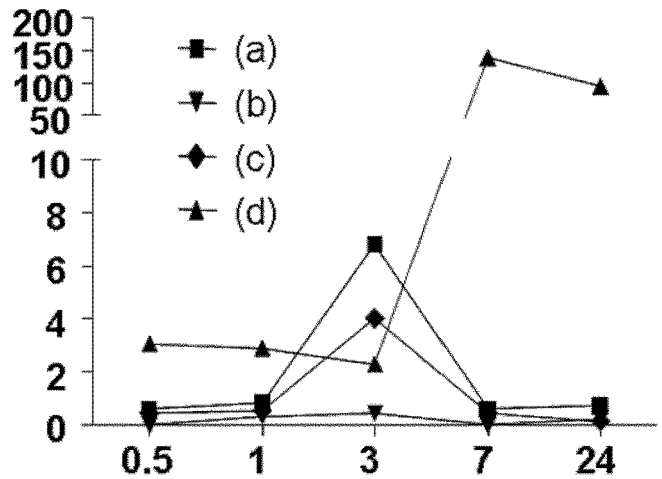
FIG. 4 shows cytokine levels over 24 hours for animals receiving different formulations of compound 'A'. The cytokines are (A) IFNγ (B) IL10 and (C) TNF.
Figure 4B:
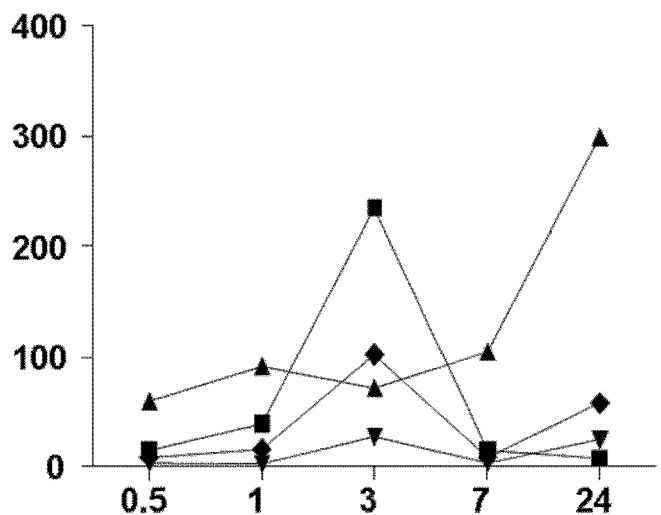
Figure 4C:
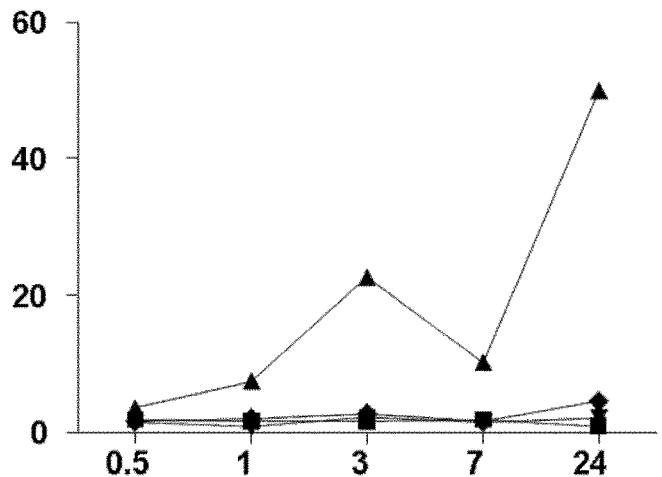

Cytokine profiles were also studied. Animals received 25 µg compound 'A' as (a) a monodispersion (c) as a monodispersion with MF59 (c) as ANE05 or (d) as ANE32. The profile for ANE32 was markedly different for IFN-γ, IL10, IL12p40, IL1b, IL5, IL6, MCP and TNF, although the levels for all groups were low and so comparisons are difficult. FIG. 4 shows three example profiles.

Immunogenicity Studies

The serogroup B meningococcus vaccine of reference 9 was tested with emulsion ANE32 as adjuvant in CD1 mice. For comparison, the same antigens were also tested with MF59, with a monodispersion of compound 'A' combined with MF59 or ANE38. ANE32 gave the highest antibody titer at day 28 (2432), but it was not significantly higher than the 'A'+MF59 group (2284). Both were higher than for the monodispersion with ANE38 (1509) or for MF59 alone (873). Although the ANE32 titer was not better than the 'A'+MF59 group, the emulsion was more stable for an extended period and so is advantageous e.g. it can be filter-sterilised, thus simplifying manufacture.

Emulsion Details and Characterisation

Specific emulsions which were tested are as follows, with a 20 ml volume:

| | |
|---|---|
| ANE05 | 4.3% sq, 0.5% S85, 0.5% T80, 10 mg 'A' |
| ANE06 | 4.3% sq, 0.5% S85, 0.5% T80, 10 mg 'A', 100 mg chol |
| ANE07 | 4.3% sq, 0.5% S85, 0.5% T80, 10 mg 'A', 100 mg chol, 100 mg POPC |
| ANE08 | 4.3% sq, 0.5% S85, 0.5% T80, 10 mg 'A', 100 mg chol, 100 mg DLPC |
| ANE09 | 4.3% sq, 0.5% S85, 0.5% T80, 10 mg 'A', 100 mg chol, 100 mg DMPC |
| ANE10 | 4.3% sq, 0.5% S85, 0.5% T80, 10 mg 'A', 100 mg chol, 100 mg DSPC |
| ANE11 | 4.3% sq, 0.5% S85, 0.5% T80, 4 mg 'A' |
| ANE12 | 2.15% sq, 0.25% S85, 0.25% T80, 10 mg 'A' |
| ANE13 | 2.15% sq, 0.25% S85, 0.25% T80, 10 mg 'A', 100 mg DLPC |
| ANE14 | 2.15% sq, 0.25% S85, 0.25% T80, 10 mg 'A', 100 mg chol, 100 mg DLPC |
| ANE15 | 2.15% sq, 0.25% S85, 0.25% T80, 10 mg 'A', 100 mg DMPC |
| ANE16 | 2.15% sq, 0.25% S85, 0.25% T80, 10 mg 'A', 100 mg chol, 100 mg DMPC |
| ANE17 | 2.15% sq, 0.25% S85, 0.25% T80, 10 mg 'A', 100 mg DSPC |
| ANE18 | 2.15% sq, 0.25% S85, 0.25% T80, 10 mg 'A', 100 mg chol, 100 mg DSPC |
| ANE19 | 4.3% sq, 0.5% S85, 0.5% T80, 10 mg 'A', 100 mg DLPC, 50 mg PVP |
| ANE20 | 4.3% sq, 0.5% S85, 0.5% T80, 10 mg 'A', 100 mg chol, 100 mg DLPC, 50 mg PVP |
| ANE21 | 4.3% sq, 0.5% S85, 0.5% T80, 10 mg 'A', 100 mg DLPC, 100 mg PVP |
| ANE22 | 4.3% sq, 0.5% S85, 0.5% T80, 10 mg 'A', 100 mg chol, 100 mg DLPC, 100 mg PVP |
| ANE23 | 4.3% sq, 0.5% S85, 0.5% T80, 10 mg 'A', 100 mg DLPC, 200 mg PVP |
| ANE24 | 4.3% sq, 0.5% S85, 0.5% T80, 10 mg 'A', 100 mg chol, 100 mg DLPC, 200 mg PVP |
| ANE31 | 4.3% sq, 0.5% S85, 0.5% T80, 10 mg 'A', 100 mg DSPC |
| ANE32 | 4.3% sq, 0.5% S85, 0.5% T80, 10 mg 'A', 100 mg DSPC, 50 mg PVP |
| ANE33 | 4.3% sq, 0.5% S85, 0.5% T80, 10 mg 'A', 50 mg PVP |
| ANE34 | 4.3% sq, 0.5% S85, 0.5% T80, 10 mg 'A', 100 mg DSPC, 50 mg PVP, 100 mg chol |
| ANE35 | 4.3% sq, 0.5% S85, 0.5% T80, 10 mg 'A', 50 mg PVP, 100 mg chol |

T80 = Tween 80; S85 = Span 85; chol = cholesterol; sq = squalene

These emulsions were generally prepared as follows. Lipophilic components (squalene, span 85, phospholipids, compound 'A') were combined in a beaker. Lipid components were dissolved in chloroform, tetrahydrofuran or dichloromethane. The oil phase was combined with the aqueous phase and immediately homogenized for 2 minute using an IKA T25 homogenizer at 24K RPM in order to provide a homogeneous feedstock. Emulsions were immediately emulsified and then allowed to sit at room temperature on a stirplate for 2-3 hours after primary homogenization in a fume hood. The primary emulsions were passed three to five times through a Microfluidizer M110S homogenizer with an ice bath cooling coil at a homogenization pressure of approximately 15 k-20 k PSI (Microfluidics, Newton, Mass.). The 20 ml batch samples were removed from the unit and stored at 4° C., and 5 ml aliquots were stored at room temperature to assess stability.

Particle size of emulsions was measured using a Zetasizer Nano ZS (Malvern Instruments,) and a LA-930 Particle Distribution Analyzer (Horiba), according to the manufacturers' guidelines. Particles were diluted in deionised water. The Horiba instrument provides d10, d50 and d90 values i.e. the diameters which divide the droplets in the sample into 10%, 50% and 90% (respectively) by mass. Results were as follows:

| | ZETA SIZER | | HORRIBA | | | | |
|---|---|---|---|---|---|---|---|
| | Particle size (nm) | Poly-dispersity | d10 (μm) | d50 (μm) | d90 (μm) | Median (μm) | Mean (μm) |
| ANE05 | 123.4 | 0.1 | 0.105 | 0.14 | 0.21 | 0.14 | 0.21 |
| ANE06 | 123.5 | 0.1 | 0.109 | 0.16 | 0.31 | 0.16 | 0.59 |
| ANE07 | 111.3 | 0.1 | 0.102 | 0.14 | 0.21 | 0.14 | 0.47 |
| ANE08 | 109.1 | 0.1 | 0.104 | 0.14 | 0.20 | 0.14 | 0.15 |
| ANE09 | 125.0 | 0.2 | 0.198 | 0.37 | 33.42 | 0.37 | 8.39 |
| ANE10 | 117.4 | 0.1 | 0.106 | 0.15 | 0.20 | 0.15 | 0.15 |
| ANE12 | 118.9 | 0.084 | 0.23 | 0.43 | 2.46 | 0.43 | 0.97 |
| ANE13 | — | — | 0.24 | 0.47 | 5.99 | 0.47 | 2.02 |
| ANE14 | — | — | 0.21 | 0.39 | 41.50 | 0.39 | 8.23 |
| ANE15 | — | — | 0.22 | 8.15 | 33.81 | 8.15 | 12.72 |
| ANE16 | 121 | 0.139 | 0.12 | 0.17 | 0.29 | 0.17 | 0.23 |
| ANE17 | 127.1 | 0.169 | 0.23 | 6.48 | 16.18 | 6.49 | 7.08 |
| ANE18 | 115.8 | 0.131 | 0.20 | 0.32 | 3.55 | 0.32 | 1.01 |
| ANE19 | 107.9 | 0.081 | 0.10 | 0.13 | 0.18 | 0.13 | 0.14 |
| ANE20 | 109.3 | 0.115 | 0.11 | 0.14 | 0.20 | 0.14 | 0.15 |
| ANE21 | 102.5 | 0.07 | 0.12 | 0.19 | 48.09 | 0.19 | 18.26 |
| ANE22 | 103.8 | 0.091 | 0.10 | 0.13 | 0.20 | 0.13 | 1.24 |
| ANE23 | 106 | 0.121 | — | — | — | — | — |
| ANE24 | 105 | 0.07 | — | — | — | — | — |
| ANE31 | 106 | 0.10 | 0.12 | 0.17 | 0.24 | 0.17 | 0.18 |
| ANE32 | 123 | 0.30 | 0.12 | 0.16 | 0.23 | 0.16 | 0.17 |
| ANE33 | 116 | 0.12 | 0.28 | 1.65 | 2.98 | 1.65 | 1.63 |
| ANE34 | 97 | 0.06 | 0.10 | 0.14 | 0.21 | 0.14 | 0.67 |
| ANE35 | 115 | 0.05 | 0.08 | 0.11 | 0.16 | 0.11 | 0.12 |

It will be understood that the invention has been described by way of example only and modifications may be made whilst remaining within the scope and spirit of the invention.

TABLE 1

| | useful phospholipids |
|---|---|
| DDPC | 1,2-Didecanoyl-sn-Glycero-3-phosphatidylcholine |
| DEPA-NA | 1,2-Dierucoyl-sn-Glycero-3-Phosphate(Sodium Salt) |
| DEPC | 1,2-Erucoyl-sn-Glycero-3-phosphatidylcholine |
| DEPE | 1,2-Dierucoyl-sn-Glycero-3-phosphatidylethanolamine |
| DEPG-NA | 1,2-Dierucoyl-sn-Glycero-3[Phosphatidyl-rac-(1-glycerol . . .) |
| DLOPC | 1,2-Linoleoyl-sn-Glycero-3-phosphatidylcholine |
| DLPA-NA | 1,2-Dilauroyl-sn-Glycero-3-Phosphate(Sodium Salt) |
| DLPC | 1,2-Dilauroyl-sn-Glycero-3-phosphatidylcholine |
| DLPE | 1,2-Dilauroyl-sn-Glycero-3-phosphatidylethanolamine |
| DLPG-NA | 1,2-Dilauroyl-sn-Glycero-3[Phosphatidyl-rac-(1-glycerol . . .) (Sodium Salt) |
| DLPG-NH4 | 1,2-Dilauroyl-sn-Glycero-3[Phosphatidyl-rac-(1-glycerol . . .) |
| DLPS-NA | 1,2-Dilauroyl-sn-Glycero-3-phosphatidylserine(Sodium Salt) |
| DMPA-NA | 1,2-Diimyristoyl-sn-Glycero-3-Phosphate(Sodium Salt) |
| DMPC | 1,2-Dimyristoyl-sn-Glycero-3-phosphatidylcholine |
| DMPE | 1,2-Dimyristoyl-sn-Glycero-3-phosphatidylethanolamine |
| DMPG-NA | 1,2-Myristoyl-sn-Glycero-3[Phosphatidyl-rac-(1-glycerol . . .) |
| DMPG-NH4 | 1,2-Myristoyl-sn-Glycero-3[Phosphatidyl-rac-(1-glycerol . . .) |
| DMPG-NH4/NA | 1,2-Myristoyl-sn-Glycero-3[Phosphatidyl-rac-(1-glycerol . . .) |
| DMPS-NA | 1,2-Dimynstoyl-sn-Glycero-3-phosphatidylserine(Sodium Salt) |
| DOPA-NA | 1,2-Dioleoyl-sn-Glycero-3-Phosphate(Sodium Salt) |
| DOPC | 1,2-Dioleoyl-sn-Glycero-3-phosphatidylcholine |
| DOPE | 1,2-Dioleoyl-sn-Glycero-3-phosphatidylethanolamine |
| DOPG-NA | 1,2-Dioleoyl-sn-Glycero-3[Phosphatidyl-rac-(1-glycerol . . .) |
| DOPS-NA | 1,2-Dioleoyl-sn-Glycero-3-phosphatidylserine(Sodium Salt) |
| DPPA-NA | 1,2-Dipalmitoyl-sn-Glycero-3-Phosphate(Sodium Salt) |
| DPPC | 1,2-Dipalmitoyl-sn-Glycero-3-phosphatidylcholine |
| DPPE | 1,2-Dipalmitoyl-sn-Glycero-3-phosphatidylethanolamine |
| DPPG-NA | 1,2-Dipalmitoyl-sn-Glycero-3[Phosphatidyl-rac-(1-glycerol . . .) |
| DPPG-NH4 | 1,2-Dipalmitoyl-sn-Glycero-3[Phosphatidyl-rac-(1-glycerol . . .) |
| DPPS-NA | 1,2-Dipalmitoyl-sn-Glycero-3-phosphatidylserine(Sodium Salt) |
| DPyPE | 1,2-diphytanoyl-sn-glycero-3-phosphoethanolamine |
| DSPA-NA | 1,2-Distearoyl-sn-Glycero-3-Phosphate(Sodium Salt) |
| DSPC | 1,2-Distearoyl-sn-Glycero-3-phosphatidylcholine |
| DSPE | 1,2-Diostearpyl-sn-Glycero-3-phosphatidylethanolamine |
| DSPG-NA | 1,2-Distearoyl-sn-Glycero-3[Phosphatidyl-rac-(1-glycerol . . .) |
| DSPG-NH4 | 1,2-Distearoyl-sn-Glycero-3[Phosphatidyl-rac-(1-glycerol . . .) |
| DSPS-NA | 1,2-Distearoyl-sn-Glycero-3-phosphatidylserine(Sodium Salt) |
| EPC | Egg-PC |
| HEPC | Hydrogenated Egg PC |
| HSPC | High purity Hydrogenated Soy PC |
| HSPC | Hydrogenated Soy PC |
| LYSOPC MYRISTIC | 1-Myristoyl-sn-Glycero-3-phosphatidylcholine |
| LYSOPC PALMITIC | 1-Palmitoyl-sn-Glycero-3-phosphatidylcholine |
| LYSOPC STEARIC | 1-Stearoyl-sn-Glycero-3-phosphatidylcholine |
| Milk Sphingomyelin MPPC | 1-Myristoyl,2-palmitoyl-sn-Glycero 3-phosphatidylcholine |
| MSPC | 1-Myristoyl,2-stearoyl-sn-Glycero-3-phosphatidylcholine |
| PMPC | 1-Palmitoyl,2-myristoyl-sn-Glycero-3-phosphatidylcholine |
| POPC | 1-Palmitoyl,2-oleoyl-sn-Glycero-3-phosphatidylcholine |
| POPE | 1-Palmitoyl-2-oleoyl-sn-Glycero-3-phosphatidylethanolamine |
| POPG-NA | 1,2-Dioleoyl-sn-Glycero-3[Phosphatidyl-rac-(1-glycerol) . . .](Sodium Salt) |
| PSPC | 1-Palmitoyl,2-stearoyl-sn-Glycero-3-phosphatidylcholine |
| SMPC | 1-Stearoyl,2-myristoyl-sn-Glycero-3-phosphatidylcholine |
| SOPC | 1-Stearoyl,2-oleoyl-sn-Glycero-3-phosphatidylcholine |
| SPPC | 1-Stearoyl,2-palmitoyl-sn-Glycero-3-phosphatidylcholine |

REFERENCES

[1] Bodmeier & Chen (1990) *J Controlled Release* 12:223-33.
[2] Tabata & Ikada (1980) *Pharm Res* 6:296-301.
[3] WO2009/111337.
[4] Yoshioka et al. (1995) *J Pharm Sci* 84:983-6.
[5] Ma e al. (1996) *Int J Pharmaceutics* 142:115-9.
[6] Jain et al. (2010) *Int J Pharmaceutics* 394:68-74.
[7] US-2007/0014805.
[8] WO2007/080308.
[9] Giuliani et al. (2006) *Proc Natl Acad Sci USA* 103(29): 10834-9.
[10] WO02/34771.
[11] WO2005/032582.
[12] WO02/34771.
[13] WO2005/002619.
[14] WO2006/138004.
[15] WO2009/109860.
[16] WO02/02606.
[17] WO03/018054.
[18] WO2006/091517.
[19] WO2008/020330.
[20] WO2006/089264.
[21] WO2009/104092.
[22] WO2009/031043.
[23] WO2007/049155.
[24] *Research Disclosure*, 453077 (January 2002).
[25] EP-A-0372501.
[26] EP-A-0378881.
[27] EP-A-0427347.
[28] WO93/17712.
[29] WO94/03208.
[30] WO98/58668.
[31] EP-A-0471177.
[32] WO91/01146.

[33] Falugi et al. (2001) *Eur J Immunol* 31:3816-3824.
[34] Baraldo et al. (2004) *Infect Immun* 72(8):4884-7.
[35] EP-A-0594610.
[36] Ruan et al. (1990) *J Immunol* 145:3379-3384.
[37] WO00/56360.
[38] WO01/72337.
[39] WO00/61761.
[40] WO00/33882
[41] Kuo et al. (1995) *Infect Immun* 63:2706-13.
[42] Michon et al. (1998) *Vaccine.* 16:1732-41.
[43] WO02/091998.
[44] *Remington: The Science and Practice of Pharmacy* (Gennaro, 2000; 20th edition, ISBN: 0683306472)

The invention claimed is:

1. An oil-in-water emulsion comprising an aqueous phase, an oil phase, a surfactant, a crystallisation inhibitor, a phospholipid and a naphthyridine TLR agonist, wherein the average droplet size in the emulsion is less than 250 nm, the naphthyridine TLR agonist has a molecular weight of less than 5000 Da and is present at a concentration sufficient to crystallize absent the crystallization inhibitor, the crystallization inhibitor is a polyvinylpyrrolidone at a concentration sufficient to inhibit crystallization of the naphthyridine TLR agonist, the phospholipid is DSPC, and >80% of the naphthyridine TLR agonist is present in the emulsion's oil droplets.

2. The emulsion of claim 1, wherein the oil phase comprises squalene.

3. The emulsion of claim 1, wherein the aqueous phase comprises a buffer.

4. The emulsion of claim 1, wherein the surfactant comprises polysorbate 80.

5. The emulsion of claim 1, comprising 2-20% (by volume) oil and 0.001%-8% (by weight) surfactant.

6. The emulsion of claim 1, wherein the weight ratio of oil to surfactant is between 4:1 and 5:1.

7. The emulsion of claim 1, comprising squalene and polysorbate 80, wherein the average diameter of the emulsion's droplets is between 80 nm and 180 nm.

8. An immunogenic composition comprising (a) the emulsion of claim 1 and (b) an immunogen.

9. The composition of claim 8, wherein the immunogen elicits an immune response in vivo against a bacterium or a virus.

10. The composition of claim 9, wherein the virus is an influenza virus.

11. The emulsion of claim 1, wherein the naphthyridine TLR agonist is a TLR7 agonist.

12. The emulsion of claim 1, wherein >90% of the naphthyridine TLR agonist is present in the emulsion's oil droplets.

* * * * *